United States Patent [19]

Sato

[11] Patent Number: 5,773,489

[45] Date of Patent: Jun. 30, 1998

[54] DENTAL INORGANIC-ORGANIC COMPOSITE FILLERS

[75] Inventor: Hisashi Sato, Tokyo, Japan

[73] Assignee: GC Corporation, Tokyo, Japan

[21] Appl. No.: 689,779

[22] Filed: Aug. 14, 1996

[30] Foreign Application Priority Data

Aug. 23, 1995 [JP] Japan ..................... 7-235987

[51] Int. Cl.$^6$ ..................... A61K 6/00
[52] U.S. Cl. ............... 523/115; 523/213; 523/216; 524/176; 524/262; 524/443; 524/450; 522/172; 526/279; 525/475; 528/9; 528/34; 501/152
[58] Field of Search ............... 528/9, 34; 523/115, 523/216, 213; 524/176, 262, 443, 450; 526/279; 522/172; 501/152; 525/475

[56] References Cited

U.S. PATENT DOCUMENTS

| | | | |
|---|---|---|---|
| 4,731,394 | 3/1988 | Vogel et al. | 523/115 |
| 5,064,877 | 11/1991 | Nass et al. | 522/172 |
| 5,132,337 | 7/1992 | Panster et al. | 524/443 |
| 5,453,456 | 9/1995 | Mitra et al. | 523/116 |
| 5,548,050 | 8/1996 | Kushibiki et al. | 528/9 |
| 5,618,872 | 4/1997 | Pohl et al. | 523/205 |

*Primary Examiner*—Andrew E.C. Merriam
*Attorney, Agent, or Firm*—Oblon, Spivak, McClelland, Maier & Neustadt, P.C.

[57] ABSTRACT

Dental inorganic-organic composite fillers are disclosed, which do not scatter a visible light of from 360 to 830 nm in the particles thereof, has a refractive index nD by the D-line of sodium in the range of $1.460 \leq nD \leq 1.600$, and which is represented by the following mean empirical formula:

$$aM^1O_{x/2} \cdot bSiO_2 \cdot cM^2O_{(4-i-j)/2}R^1{}_iR^2{}_j$$

wherein $M^1$ is one or more members selected from Ti, Zr, Y, La, Ta, and Al, which is bonded to Si or M2 via the crosslinked oxygen; and x is a valence of $M^1$;

$M^2$ is Si and/or Ti;

$R^1$ is a non-functional group; and $R^2$ is an organic compound reacted with an organic functional group;

i is 0, 1, or 2; and j is 1, 2, or 3, provided that i and j are satisfied with $1 \leq (i+j) \leq 3$; and a, b, and c are each a molar ratio, provided that a, b, and c are satisfied with $0 \leq a/(a+b) \leq 0.65$ and $0.02 \leq c/(a+b) \leq 3.0$.

5 Claims, No Drawings

DENTAL INORGANIC-ORGANIC COMPOSITE FILLERS

FIELD OF THE INVENTION

The present invention relates to fillers which are used for dental restorative materials. The fillers according to the present invention are mixed with polymerizable monomers, polymerization catalysts, and the like and then provided for dental restorative materials. The dental restorative materials as referred to in the present invention are called as a dental composite resin and mean tooth-filling restorative materials, coronal prostheses such as inlays, crowns, and bridges, denture materials, and abutment tooth construction materials.

BACKGROUND OF THE INVENTION

Hitherto, fillers which are mixed with polymerizable monomers and polymerization catalysts and then provided for dental restorative materials are roughly classified as follows.

Filler (1)

Ground products of synthetic or natural inorganic compounds such as quartz, silica glass, alkali and alkaline-earth metal aluminosilicate glasses, alkali and alkaline-earth metal aluminoborosilicate glasses, alkaline-earth metal aluminosilicate glasses, and alkaline-earth metal aluminoborosilicate glasses Filler (2)

Spherical powders of silica or silicate glasses prepared by the sol-gel process or self-combustion of metals Filler (3)

Colloidal silica having a size in the nanometers order, prepared by the vapor phase process Filler (4)

Ground products of inorganic-organic composite compounds prepared by mixing succeeding polymerizing the above-described fillers (1), (2), or (3) with polymerizable monomers Filler (5)

Inorganic-organic composite capsulated powders comprising the above-described fillers (1), (2), or (3) as a core and polymerizable monomers as a coating material Filler (6)

Organic fillers such as PMMA containing no inorganic filler

Others

Fillers in which the surfaces of the above-described fillers (1), (2), or (3) are modified with a processing agent to improve the wettability with polymerizable monomers to be mixed or a processing agent capable of reacting therewith.

Depending on the purposes for the use of dental restorative materials, various kinds of fillers, polymerizable monomers, and polymerization initiators are properly selected, and the various functions as described below are imparted according to the respective purposes.

Suitable consistency and handling
mechanical strength
Low polymerization shrinkage
Abrasion resistance
Coefficient of thermal expansion close to that of the teeth
Suitable transparency
Surface smoothness Though the above-described ground products of inorganic compounds as the filler (1) contribute to the suitable consistency and handling, the mechanical strength, the low polymerization shrinkage, the coefficient of thermal expansion close to that of the teeth, and the suitable transparency, they adversely affect the surface smoothness, resulting in lowering the abrasion resistance. Though fillers having a maximum particle size of 2 $\mu$m and a mean particle size of from about 0.1 to 0.9 $\mu$m (so-called "submicron fillers"), which have been used in the recent years, impart the surface smoothness like that of the natural teeth immediately after the restoration, their smoothness is lost in the cavity with time. Also, since the "submicron fillers" are much fine, its functions concerning the low polymerization shrinkage and the coefficient of thermal expansion close to the teeth tend to lower.

Though the spherical powders of glass as the filler (2) contribute to the manifestation of the mechanical strength, the abrasion resistance, the coefficient of thermal expansion close to that of the teeth, and the surface smoothness, they have no superiority with respect to the low polymerization shrinkage and the suitable transparency. Preparations of the filler (2) with adequate refractive indexes are difficult. So if there are differences in refractive indexes between the fillers and matrixes, resulting dental restorative materials become opaque. In particular, in case that the fillers are more finely prepared than the filler (1), the resulting dental restorative materials become opaque. The filler (2) scatters a light having a specific wavelength in visible lights within a prescribed particle size range and imparts a peculiar opacity (opalescence). For this reason, the amount of the filler (2) is small to keep the transparency necessary for the dental restorative materials, and the filler (2) is generally used in combination with the filler (1). Also, the kind of the polymerizable monomers which can be used is restricted.

Though the colloidal silica as the filler (3) contributes to the suitable consistency and handling and the surface smoothness, it can not be expected to manifest other functions. The filler (3) imparts the opalescence like the filler (2) within a prescribed particle size range. The filler (3) plays an auxiliary part of the filler (1).

Though the ground products of inorganic-organic composite compounds as the filler (4) and the inorganic-organic composite capsulated powders as the filler (5) contribute to the suitable consistency and handling and the low polymerization shrinkage, since they can not overcome the defects of the inorganic fillers to be contained, not only the characteristics of the filler (1) as described above remain and they are disadvantageous in obtaining the coefficient of thermal expansion close to that of the teeth.

Though the organic fillers as the filler (6) contribute to the suitable consistency and handling, the low polymerization shrinkage, the suitable transparency, and the surface smoothness, they do not contribute at all to the manifestation of the mechanical strength and the abrasion resistance.

That is, the inorganic fillers having a size exceeding the submicrons order are different greatly in hardness from the matrix resin so that their abrasion rate in the oral cavity is different from that of the latter. Therefore, unevenness is generated on the surfaces, and the falling of the fillers takes place, whereby the surface smoothness is lost. Also, since the preparations of much fine spherical inorganic fillers with adequate refractive indexes are difficult, if there is a difference in the refractive index from the matrix resin, they impart the opalescence. So their amount of use is actually restricted. In addition, the fine colloidal silica having a size in the nanometers order is poor in its mechanical reinforcement effect and is abraded together with the matrix resin.

As other fillers, there is a so-called [alkoxide+coupling agent] type filler as spherical or spheroidal particles obtained in si-tu by co-hydrolysis of metal alkoxides and organic functional group-containing metal alkoxides, as disclosed in Japanese Patent Application Laid-Open No. 2-248315, Japanese Patent Application Laid-Open No. 2-225302, and Japanese Patent Application Laid-Open No. 2-288816. These particles have organic functional groups in the interiors and on the surfaces and when they are used as a filler for dental restorative materials, only the organic functional groups exposed on the surfaces can react with the matrix resin. This filler is identical to one obtained by subjecting an existing inorganic filler to the surface treatment with an organic functional group-containing alkoxysilane generally called as a silane coupling agent and is corresponding to the above-described filler (2).

Besides, there is a so-called [(alkoxide+coupling agent) +organic compound] type filler as inorganic-organic composite spherical or spheroidal particles prepared by co-hydrolysis of metal alkoxides and organic functional group-containing metal alkoxides to form in si-tu spherical or spheroidal particles, which are then added with vinyl monomers and grafted while polymerizing in the presence of a radical polymerization catalyst, as disclosed in Japanese Patent Application Laid-Open No. 4-15209. However, while the filler as disclosed in this patent is novel with respect to the preparation process, it is corresponding to the above-described filler (5), and there is an intergranule between the inorganic compound and the organic compound.

In the light of the above, according to the conventional technology, fillers thoroughly provided with functions so as to keep the surface smoothness even after the abrasion, mechanically reinforce the matrix resin, and impart the transparency to the dental restorative materials have not yet been developed.

SUMMARY OF THE INVENTION

Therefore, the present invention has been aimed to provide novel dental inorganic-organic composite fillers which not only overcome the above-described defects of the conventional fillers in case that they are used for dental restorative materials to improve the functions, i.e. to keep the surface smoothness in the oral cavity, mechanically reinforce the matrix resin, and impart the transparency, but also can be satisfied with all of the above-described functions required for the dental restorative materials.

As results, the present inventor has obtained inorganic-organic composite fillers by reacting inorganic components with organic components during the synthesis from a metal alkoxide without using any existing inorganic fillers as the inorganic components to obtain inorganic-organic composite compounds, which are then ground. As the results of using the inorganic-organic composite fillers for dental restorative materials, the above-described various functions required for the dental restorative materials can be satisfied.

That is, the dental inorganic-organic composite fillers according to the present invention are dental inorganic-organic composite fillers which do not scatter a visible light of from 360 to 830 nm in the particles thereof since no intergranule is present, have a refractive index nD by the D-line of sodium in the range of $1.460 \leq nD 51.600$, and which is represented by the following mean empirical formula:

$$aM^1O_{x/2} \cdot bSiO_2 \cdot CM^2O_{(4-i-j)/2}R^1_i R^2_j$$

wherein $M^1$ is one or more members selected from Ti, Zr, Y, La, Ta, and Al, which is bonded to Si or $M^2$ via the crosslinked oxygen; and x is a valence of $M^1$;

$M^2$ is Si and/or Ti;

$R^1$ is a non-functional group; and $R^2$ is an organic compound reacted with an organic functional group;

i is 0, 1, or 2; and j is 1, 2, or 3, provided that i and j are satisfied with $1 \leq (i+j) \leq 3$; and a, b, and c are each a molar ratio, provided that a, b, and c are satisfied with $0 \leq a/(a+b) \leq 0.65$ and $0.02 \leq c/(a+b) \leq 3.0$.

DETAILED DESCRIPTION OF THE INVENTION

The components in the above-described mean empirical formula are described below in detail.

$M^1O_x/2$ represents derivatives of an alkoxide, acetylacetonato, nitrate, or acetate of Ti, Zr, Y, La, Ta, or Al, wherein x is a valence of $M^1$. As the alkoxides of various metals, various alkoxides such as methoxides, ethoxides, n-propoxides, isopropoxides, n-butoxides, and tert-butoxides can be exemplified. As these materials, commercially available products, or alcoholic solutions of alkoxides obtained by the reaction of metals and alcohols can be used. Zr, La, and Al for the acetylacetonato, Ti, Y, La, and Al for the nitrate, and Y, La, and Al for the acetate are available as commercial products, respectively. Since ones other than these metals are generally expensive, or have such properties that they tend to be precipitated in the sol-gel process, readily form an interface, or are readily colored, they are unsuitable for the introduction into the dental restorative materials. Also, for the same reasons, even when $M^1$ is Ti, Zr, Y, La, Ta, or Al, there is a limitation in the range of $0 \leq a/(a+b) \leq 0.65$. Incidentally, in case that the dental restorative materials are prepared by using the dental inorganic-organic composite fillers according to the present invention, when it is required to impart the X-ray contrast properties to the dental restorative materials, it is preferred that $M^1$ is one or more members selected from Zr, Y, La, and Ta and that a and b are satisfied with $0.10 \leq a/(a+b) \leq 0.65$.

$SiO_2$ is a derivative of an alkoxide of Si, and methoxides, ethoxides, n-propoxides, iso-propoxides, n-butoxides, tert-butoxides, and the like can be exemplified. From dimers to hexamers of alkoxides thereof can also be used.

$aM^1O_{x2} \cdot bSiO_2 \cdot cM^2O_{(4-i-j)/2}R^1_i R^2_j$ represents derivatives reactive alkoxysilanes generally called as silane coupling agents, when $M^2$ is Si. Examples of alkoxysilanes having an unsaturated double bond include 3-methacryloxypropyl trimethoxysilane, 3-methacryloxypropyl triethoxysilane, 3-acryloxypropyl trimethoxysilane, 3-methacryloxypropylmethyl dimethoxysilane, 3-methacryloxypropylmethyl diethoxysilane, 3-acryloxypropylmethyl dimethoxysilane, 2-methacryloxy-ethoxypropyl trimethoxysilane, vinyl trimethoxysilane, vinyl triethoxysilane, and vinyl tris(2-methoxyethoxy) silane. Examples of alkoxysilanes having a glycidoxyl group include 2-(3,4-epoxycyclohexyl)ethyl trimethoxysilane, 3-glycidoxypropyl trimethoxysilane, 3-glycidoxypropylmethyl dimethoxysilane, 3-glycidoxypropylmethyl diethoxysilane, and 3-glycidoxypropyl triethoxysilane. Examples of alkoxysilanes having an amino group include N-2-(aminoethyl)-3-aminopropyl trimethoxysilane, N-2-(aminoethyl)-3-aminopropyl triethoxysilane, 3-aminopropyl trimethoxysilane, 3-aminopropyl triethoxysilane, and N-phenyl-3-aminopropyl trimethoxysilane. Examples of alkoxysilanes having a mercapto group include 3-mercaptopropyl trimethoxysilane and 3-mercaptopropyl triethoxysilane. Examples of alkoxysilanes having an alkoxyl group include methyl trimethoxysilane, dimethyl dimethoxysilane, phenyl trimethoxysilane, diphenyl dimethoxysilane, methyl triethoxysilane, dimethyl diethoxysilane, phenyl triethoxysilane, diphenyl dimethoxysilane, isobutyl trimethoxysilane, and decyl trimethoxysilane, in addition to the above-exemplified compounds. The alkoxyl group and/or silanol group of the above-described coupling agent are/is reacted with derivatives of various alkoxides, acetylacetonatos, nitrates, or acetates of Ti, Zr, Y, La, Ta, or Al represented by $M^1O_{x/2}$, wherein x is a valence of $M^1$, and/or various alkoxide derivatives of Si.

$aM^1O_{x/2} \cdot bSiO_2 \cdot cM^2O_{(4-i-j)/2}R^1_iR^2_j$ represents derivatives of a reactive alkoxytitanium generally called as titanate coupling agents, when $M^2$ is Ti. Examples of titanate coupling agents having an unsaturated double bond include isopropyl dimethacrylisostearoyl titanate, isopropyl diacrylisostearoyl titanate, isopropyl trimethacryl titanate, isopropyl triacryl titanate, oxyacetyl dimethacryl titanate, and oxyacetyl diacryl titanate. Examples of titanate coupling agents having an amino group include isopropyl tri(N-diethylamino) titanate, isopropyl tri(2-aminobenzoyl) titanate, isopropyl tri(tetraethylenetriamine) titanate, isopropyl 4-aminobenzenesulfonyl di(dodecylbenzenesulfonyl) titanate, and isopropyl di(4-aminobenzoyl)isostearoyl titanate. The alkoxyl group and/or titanol group of the above-described coupling agent are/is reacted with derivatives of various alkoxides, acetylacetonatos, nitrates, or acetates of Ti, Zr, Y, La, Ta, or Al represented by $M^1O_{x/2}$, wherein x is a valence of $M^1$, and/or various alkoxide derivatives of Si.

$R^1$ is a phenyl group and/or a non-functional group represented by $C_nH_{2n+1}$, wherein n is from 1 to 10.

$R^2$ is an organic compound reacted with a functional group selected from the unsaturated double bond, the glycidoxyl group, the amino group, the mercapto group, or the alkoxyl group of the silane coupling agent and/or the titanate coupling agent. For this reason, if the amount of the coupling agents is too small, the introduced organic compound tends to form an intergranule alone without reacting with the functional group of the coupling agents. On the other hand, if the amount of the coupling agents is too large, the functional group of the coupling agents tends to remain in the particles, whereby the strength as the filler is lowered. Therefore, the ratio of the coupling agents is limited in the range of $0.02 \leq c/(a+b) \leq 3.0$.

Also, when $M^2$ is Si, then $R^2$ is an organic compound reacted with a functional group selected from the unsaturated double bond, the glycidoxyl group, the amino group, the mercapto group, or the alkoxyl group, or when $M^2$ is Ti, then $R^2$ is an organic compound reacted with a functional group selected from the unsaturated double bond or the amino group; and $R^1$ is a phenyl group and/or a non-functional group represented by $C_nH_{2n+1}$, wherein n is from 1 to 10.

Examples of organic compounds to react with the unsaturated double bond of the coupling agent include unsaturated polyesters and resins of monomers having an unsaturated double bond such as methyl methacrylate, ethyl methacrylate, isopropyl methacrylate, 2-hydroxyethyl methacrylate, 3-hydroxypropyl methacrylate, 2-hydroxy-1, 3-dimethacryloxypropane, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, benzyl methacrylate, phenyl methacrylate, phenoxyethyl methacrylate, 2,2-bis(methacryloxyphenyl)propane, 2,2-bis [4-(2-hydroxy-3-methacryloxypropoxy)phenyl)propane, 2,2-bis(4-methacryloxy-diethoxyphenyl]propane, 2,2-bis(4-methacryloxypolyethoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylol-propane trimethacrylate, trimethylolethane trimethacrylate, pentaerythritol trimethacrylate, trimethylolmethane trimethacrylate, pentaerythritol tetramethacrylate, and corresponding acrylates thereto, and methacrylates or acrylates having a urethane bond in the molecule thereof, e.g., di-2-methacryloxyethyl-2,2,4-trimethylhexamethylene dicarbamate and a corresponding acrylate thereto. Since these methacrylates and acrylates are known as dental materials, they are used alone or in admixture, if desired.

Examples of organic compounds to react with the glycidoxyl group of the coupling agent include epoxy resins, alcoholic hydroxyl group-containing resins such as phenol resins, amine-based compounds such as aliphatic polyamines, polyamide resins, and aromatic diamines, mixtures of amine-based compounds with epoxy resins, compounds having an unsaturated double bond and a glycidyl group such as glycidyl methacrylate and allyl glycidyl ether, and mixtures thereof with epoxy resins. They are used alone or in admixture, if desired.

Examples of organic compounds to react with the amino group of the coupling agent include epoxy resins, phenol resins, compounds having an unsaturated double bond and a glycidyl group such as glycidyl methacrylate and allyl glycidyl ether, compounds having an isocyanate group, and/or mixtures thereof with polyols. They are used alone or in admixture, if desired.

Examples of organic compounds to react with the mercapto group of the coupling agent include the above-described compounds having an unsaturated double bond alone and/or mixtures thereof, compounds having an isocyanato group, and/or mixtures thereof with polyols.

Examples of organic compounds to react with the alkoxyl group of the coupling agent include epoxy resins having a hydroxyl group, polymers and/or copolymers having a carboxyl group such as polyacrylic acid, polymaleic acid, and polyitaconic acid, polyols methacrylates and/or acrylates having a hydroxyl group and an unsaturated double bond alone, such as 2-hydroxyethyl methacrylate, 3-hydroxypropyl methacrylate, 2-hydroxyl-1,3-dimethacryloxypropane, hydroxy-propyl methacrylate, and 2,2-bis[4-(2-hydroxy-3-methacryl-oxypropoxy)phenyl] propane, and/or mixtures thereof. In case that the organic functional group is an alkoxyl group, tetraethoxysilane, tetramethoxysilane, and the like can be used without using the coupling agent. In this case, the mean empirical formula according to the present invention is corresponding to one represented by the following formula:

$$aM^1O_{x/2} \cdot bSiO_2 \cdot cM^2O_{(4-i-j)/2}R^1_iR^2_j$$

wherein $M^2$ is Si; i is 0; and i is 1, 2, or 3.

The organic compounds as exemplified above are known as general purpose resins and are available from various companies such as Yuka Shell Epoxy Co., Ltd., Mitsui Petrochemical Industries, Ltd., Dainippon Ink and Chemicals, Inc., Sumitomo Chemical Co., Ltd., Sumitomo Bayer Urethane Co., Ltd., NOF Corporation, Nippon Kayaku Co., Ltd., Mitsubishi Gas Chemical Company, Inc., and Mitsubishi Rayon Co., Ltd., and catalogs, "Plastics Material Lectures" published by Nikkan Kogyo Shinbunsha, "Chemical Products Inquiries" published by Kagaku Kogyo Nipposha, and the like can be referred to.

In case that the dental inorganic-organic composite fillers according to the present invention are mixed with polymerizable monomers, polymerization catalysts, and the like and then provided for dental restorative materials, when the polymerizable monomers to be mixed are a compound having an unsaturated double bond, it is suitable that the particle surfaces are modified by a silane coupling agent as the processing agent which can improve the wettability or can be reacted. Examples of the processing agent which can improve the wettability or can be reacted include silane coupling agents. Especially, 3-methacryloxypropyl trimethoxysilane, 3-methacryloxypropyl triethoxysilane, 3-acryloxypropyl trimethoxysilane, 3-methacryloxypropylmethyl dimethoxysilane, 3-methacryloxypropylmethyl diethoxysilane, 3-acryloxypropylmethyl dimethoxysilane, 2-methacryloxyethoxypropyl trimethoxysilane, vinyl trimethoxysilane, vinyl triethoxysilane, vinyl tris(2-methoxyethoxy)silane, 2-(3,4-epoxycyclohexyl)ethyl trimethoxysilane, 3-glycidoxypropyl trimethoxysilane, 3-glycidoxypropylmethyl dimethoxysilane, 3-glycidoxypropylmethyl diethoxysilane, 3-glycidoxypropyl triethoxysilane, N-2-(aminoethyl)-3-aminopropyl trimethoxy-silane, N-2-(aminomethyl)-3-aminopropyl triethoxysilane, 3-aminopropyl trimethoxysilane, 3-aminopropyl triethoxysilane, N-phenyl-3-aminopropyl trimethoxysilane, 3-mercaptopropyl trimethoxysilane, and 3-mercaptopropyl triethoxysilane are useful.

In case that the dental inorganic-organic composite fillers according to the present invention are provided for dental restorative materials, one of the important functions is suitable transparency. When the dental inorganic-organic composite filler according to the present invention has a refractive index nD by the D-line of sodium in the range of $1.460 \leq nD \leq 1.600$, it can impart a suitable transparency such that it can withstand against the practical use for dental restorative materials. Also, in order that the dental restorative materials keep the surface smoothness even after the abrasion and that the reinforcement effect as the filler can be remarkably manifested, it is preferred that the amount of the inorganic component in the filler is from 10 to 80% by weight. In addition, in case that the filler has a mean particle size of from 0.1 to 50 μm, the filling characteristics of the filler in the dental restoration and the finished polished surface become good and hence, such is preferred.

The present invention is further described below with reference to the following examples.

[COMMON CONDITIONS]

Ethoxides (abbreviated as OEt) for Si and Ta, isopropoxides (abbreviated as Oipr) for Ti, Y, La, and Al, and an n-butoxide (abbreviated as OnBu) for Zr were respectively used. The compositions are summarized and described in Table 1. The hydrolysis of the various alkoxides was carried out at room temperature, and the maturing was carried out at 90° C.

Solution (1)

In a dried nitrogen atmosphere, distilled and dehydrated t-butyl alcohol (abbreviated as t-BuOH) and silicon tetraethoxide (abbreviated as TEOS) were weighed and added dropwise with an acidic aqueous solution of t-butyl alcohol in a flask equipped with a reflux condenser, to prepare Solution (1).

Solution (2)

In a dried nitrogen atmosphere, distilled and dehydrated t-butyl alcohol and each of the metal alkoxides were weighed and added dropwise to Solution (1) while stirring, and distilled water was then added dropwise thereto under the reflux conditions while heating, to prepare Solution (2).

EXAMPLE 1

In a dried nitrogen atmosphere, distilled and dehydrated t-butyl alcohol and 3-methacryloxypropyl trimethoxysilane (abbreviated as 3MtPTMeS) were weighed and added dropwise with an acidic aqueous solution of t-butyl alcohol in a flask equipped with a reflux condenser and an agitator. The mixture was added dropwise with Solution (1) and then with distilled water. The mixture was further added with 2,2-bis (4-methacryloxypolyethoxyphenyl)propane (abbreviated as Bis-MEPP) and triethylene glycol dimethacrylate (abbreviated as TEGDMA) under the reflux conditions while heating. In addition, the mixture was added with a solution of azobisisobutyronitrile in t-butyl alcohol, followed by adding dropwise a basic aqueous solution of t-butyl alcohol thereto to gel the whole of the solution. The gel was matured under the reflux conditions while heating, ground, and then washed with methanol. The product was dried with heating under reduced pressure flowing a dried nitrogen gas to obtain inorganic-organic composite fillers.

70 parts by weight of the powder having 1 part by weight of 3-methacryloxypropyl trimethoxysilane added thereto was kneaded under vacuum with 30 parts by weight of a mixed monomer of di-2-methacryloxyethyl-2,2,4-trimethyl-hexamethylene dicarbamate (abbreviated as UDMA), TEGDMA, and Bis-MEPP containing 0.1 part by weight of camphorquinone and 0.5 part by weight of dimethylamino-methacrylate, which had been adjusted so as to have a refractive index after the curing close to the inorganic-organic composite filler, to prepare a dental restorative material, which was then provided for the tests. The results are summarized in Table 1.

EXAMPLES 2 TO 8

In a dried nitrogen atmosphere, distilled and dehydrated t-butyl alcohol and 3-methacryloxypropyl trimethoxysilane were weighed and added dropwise with an acidic aqueous solution of t-butyl alcohol in a flask equipped with a reflux condenser and an agitator. The mixture was added dropwise with Solution (2) prepared by using each of the metal alkoxides as shown in Table 1 and then with distilled water. After the maturing, the mixture was added with Bis-MEPP and TEGDMA. In addition, the mixture was added dropwise with a solution of azobisisobutyronitrile (0.5 part by weight based on the sum of the monomers, hereinafter the same) in t-butyl alcohol, followed by adding dropwise a basic aqueous solution of t-butyl alcohol thereto to gel the whole of the solution. The gel was matured under the reflux conditions while heating, ground, and then washed with methanol. The product was dried with heating under reduced pressure flowing a dried nitrogen gas to obtain inorganic-organic composite fillers. Dental restorative materials were prepared by using each of these fillers in the same manner as in Example 1, which were than provided for the tests. The results are summarized in Table 1 and 2.

EXAMPLES 9 AND 10

In the preparation of the inorganic-organic composite fillers, methyl methacrylate (abbreviated as MMA) was introduced as the organic compound in accordance with the method of Example 2, to obtain inorganic-organic composite fillers. Dental restorative materials were prepared in the same manner as in Example 1 and then provided for the tests. The results are summarized in Table 2.

EXAMPLES 11 AND 12

In the preparation of the inorganic-organic composite fillers, a mixture of MMA and benzyl methacrylate (abbreviated as BZMA) was introduced as the organic compound in accordance with the method of Example 3, to obtain inorganic-organic composite fillers. Dental restorative materials were prepared in the same manner as in Example 1 and then provided for the tests. The results are summarized in Table 3.

EXAMPLES 13 TO 15

In the preparation of the inorganic-organic composite filler, the same manner as in Example 2 was followed, except that the compounding ratio was changed, to obtain inorganic-organic composite fillers. Dental restorative materials were prepared in the same manner as in Example 1 and then provided for the tests. The results are summarized in Table 3.

EXAMPLES 16 AND 17

In the preparation of the inorganic-organic composite filler, the same substances to be contained as those used in Example 1 were used, except that only the grinding conditions were changed, to obtain inorganic-organic composite fillers. Dental restorative materials were prepared in the same manner as in Example 1 and then provided for the tests. The results are summarized in Table 4.

EXAMPLE 18

In a dried nitrogen atmosphere, distilled and dehydrated t-butyl alcohol and 3-methacryloxypropylmethyl dimethoxysilane (abbreviated as 3MtPMDMeS) were weighed and added dropwise with an acidic aqueous solution of t-butyl alcohol in a flask equipped with a reflux condenser and an agitator. The mixture was added dropwise with Solution (1) and then with distilled water. The mixture was further added with Bis-MEPP and TEGDMA under the reflux conditions while heating. In addition, the mixture was added with a solution of azobisisobutyronitrile in t-butyl alcohol, followed by adding dropwise a basic aqueous solution of t-butyl alcohol thereto to gel the whole of the solution. The gel was matured under the reflux conditions while heating, ground, and then washed with methanol. The product was dried with heating under reduced pressure flowing a dried nitrogen gas to obtain inorganic-organic composite fillers. A dental restorative material was prepared by using this filler in the same manner as in Example 1, which was then provided for the tests. The results are summarized in Table 4.

EXAMPLE 19

In a dried nitrogen atmosphere, distilled and dehydrated dimethyl ketone, 2,2-bis(4-glycidyloxyphenyl)propane (abbreviated as BisGPhP), and 3-glycidyloxypropyl trimethoxysilane (abbreviated as 3GPTMeS) were weighed and added dropwise with a solution of a polyamide resin having an amine value of 210 (abbreviated as Polyamide) in dimethyl ketone in a flask equipped with a reflux condenser and an agitator. The mixture was added dropwise with Solution (2) under the reflux conditions while heating and then with a basic aqueous solution of dimethyl ketone to gel the whole of the solution. The gel was matured under the reflux conditions while heating, ground, and then washed with methanol. The product was dried with heating under reduced pressure flowing a dried nitrogen gas to obtain inorganic-organic composite fillers.

70 parts by weight of the powder having 1 part by weight of 3-methacryloxypropyl trimethoxysilane added thereto was kneaded under vacuum with 30 parts by weight of a mixed monomer of UDMA and neopentyl glycol dimethacrylate (abbreviated as NPGDMA) containing 0.1 part by weight of camphorquinone and 0.5 part by weight of dimethyl-aminomethacrylate, which had been adjusted so as to have a refractive index after the curing close to that of the inorganic-organic composite filler, to prepare a dental restorative material, which was then provided for the tests. The results are summarized in Table 4.

EXAMPLE 20

In a dried nitrogen atmosphere, distilled and dehydrated dimethyl ketone and 3-aminopropyl trimethoxysilane (abbreviated as 3APTMeS) were weighed and added dropwise with glycidyl methacrylate (abbreviated as GMA) in a flask equipped with a reflux condenser and an agitator. The mixture was added dropwise with Solution (2) under the reflux conditions while heating, followed by adding Bis-MEPP and TEGDMA thereto. The mixture was added dropwise with a solution of azobisisobutyronitrile in dimethyl ketone and then with a basic aqueous solution of dimethyl ketone to gel the whole of the solution. The gel was matured under the reflux conditions while heating, ground, and then washed with methanol. The product was dried with heating under reduced pressure flowing a dried nitrogen gas to obtain inorganic-organic composite fillers. Also, a dental restorative material was prepared in the same manner as in Example 19, while using a mixed monomer of Bis-MEPP and TEGDMA, which was then provided for the tests. The results are summarized in Table 4.

EXAMPLE 21

In a dried nitrogen atmosphere, distilled and dehydrated t-butyl alcohol and 3-mercaptopropyl trimethoxysilane (abbreviated as 3McPTMeS) were weighed and added dropwise with an acidic aqueous solution of t-butyl alcohol to undergo the hydrolysis in a flask equipped with a reflux condenser and an agitator. The mixture was added dropwise with Solution (2), followed by adding Bis-MEPP and TEGDMA thereto under the reflux conditions while heating. The mixture was added dropwise with a solution of azobisisobutyronitrile in t-butyl alcohol and then with a basic aqueous solution of t-butyl alcohol to gel the whole of the solution. The gel was matured under the reflux conditions while heating, ground, and then washed with methanol. The product was dried with heating under reduced pressure flowing a dried nitrogen gas to obtain inorganic-organic composite fillers. Also, a dental restorative material was prepared in the same manner as in Example 20, which was then provided for the tests. The results are summarized in Table 5.

EXAMPLE 22

In a dried nitrogen atmosphere, distilled and dehydrated dimethyl ketone, phenyl trimethoxysilane (abbreviated as PhTMeS), 1,3-butanediol (abbreviated as 1,3BG), and p-toluenesulfonic acid were weighed, and the mixture was refluxed while heating at 110° C. in a flask equipped with a flux condenser and an agitator. After cooling to 60° C., the mixture was added dropwise with Solution (2) and then refluxed. The resulting mixture was added dropwise with a basic aqueous solution of t-butyl alcohol to gel the whole of the solution. The gel was matured under the reflux conditions while heating, ground, and then washed with methanol. The product was dried with heating under reduced pressure flowing a dried nitrogen gas to obtain inorganic-organic composite fillers. Also, a dental restorative material was prepared in the same manner as in Example 19, which was then provided for the tests. The results are summarized in Table 5.

EXAMPLE 23

In a dried nitrogen atmosphere, distilled and dehydrated dimethyl ketone, diphenyl dimethoxysilane (abbreviated as DPhDMeS), 1,3BG, and p-toluenesulfonic acid were weighed, and the mixture was refluxed while heating at 110° C. After cooling to 60° C. in a flask equipped with a flux device and an agitator, the mixture was added dropwise with Solution (2) and then refluxed. The resulting mixture was added dropwise with a basic aqueous solution of t-butyl alcohol to gel the whole of the solution. The gel was matured under the reflux conditions while heating, ground, and then washed with methanol. The product was dried with heating under reduced pressure flowing a dried nitrogen gas to obtain inorganic-organic composite fillers. Also, a dental restorative material was prepared in the same manner as in Example 19, which was then provided for the tests. The results are summarized in Table 5.

EXAMPLE 24

In a dried nitrogen atmosphere, distilled and dehydrated t-butyl alcohol and isopropyl trimethacryloyl titanate (abbreviated as IPTMtT) were weighed and added dropwise with an acidic aqueous solution of t-butyl alcohol to undergo the hydrolysis in a flask equipped with a reflux condenser and an agitator. The mixture was added dropwise with Solution (2), followed by adding Bis-MEPP and TEGDMA thereto under the reflux conditions while heating. The mixture was added dropwise with a solution of azobisisobutyronitrile in t-butyl alcohol and then with a basic aqueous solution of t-butyl alcohol to gel the whole of the solution. The gel was matured under the reflux conditions while heating, ground, and then washed with methanol. The product was dried with heating under reduced pressure flowing a dried nitrogen gas to obtain inorganic-organic composite fillers. Also, a dental restorative material was prepared in the same manner as in Example 20, which was then provided for the tests. The results are summarized in Table 5.

EXAMPLE 25

In a dried nitrogen atmosphere, distilled and dehydrated dimethyl ketone and isopropyl tri(N-diethylamino) titanate (abbreviated as IPTAT) were weighed and added dropwise with glycidyl methacrylate under the reflux conditions while heating in a flask equipped with a reflux condenser and an agitator. The mixture was added dropwise with Solution (2) under the reflux conditions while heating, followed by adding Bis-MEPP and TEGDMA thereto. The mixture was added dropwise with a solution of azobisisobutyronitrile in dimethyl ketone and then with a basic aqueous solution of dimethyl ketone to gel the whole of the solution. The gel was matured under the reflux conditions while heating, ground, and then washed with methanol. The product was dried with heating under reduced pressure flowing a dried nitrogen gas to obtain inorganic-organic composite fillers. Also, a dental restorative material was prepared in the same manner as in Example 19, which was then provided for the tests. The results are summarized in Table 5.

COMPARATIVE EXAMPLE 1

2 parts by weight of 3-methacryloxypropyl trimethoxysilane was added to ground products of an alkaline-earth metal aluminoborosilicate glass having a mean particle size of 1 $\mu$m to form a filler. 70 parts by weight of this powder was kneaded under vacuum with 30 parts by weight of a mixed monomer of Bis-MEPP and TEGDMA containing 0.1 part by weight of camphorquinone and 0.5 part by weight of dimethylaminomethacrylate, to prepare a dental restorative material, which was then provided for the tests. The results are summarized in Table 5.

COMPARATIVE EXAMPLE 2

In a dried nitrogen atmosphere, ethanol was weighed and added dropwise with silicon tetraethoxide and a basic aqueous solution of ethanol separately but simultaneously while stirring in a flask equipped with a reflux condenser and an agitator. The thus obtained spherical particles were washed with distilled water and then dried at 400° C. to form a filler. 62 parts by weight of the powder having 4 parts by weight of 3-methacryloxypropyl trimethoxysilane added thereto was kneaded under vacuum with 38 parts by weight of a mixed monomer of UDMA and TMPTMA containing 0.1 part by weight of camphorquinone and 0.5 part by weight of dimethylamino-methacrylate, to prepare a dental restorative material, which was then provided for the tests. The results are summarized in Table 5.

COMPARATIVE EXAMPLE 3

As colloidal silica having a size in the nanometers order to be prepared by the vapor phase process, R972 made by Nippon Aerosil Co., Ltd. was used and provided for fillers. 48 parts by weight of this powder was kneaded under vacuum with 52 parts by weight of a mixed monomer of UDMA and TMPTMA containing 0.1 part by weight of camphorquinone and 0.5 part by weight of dimethylaminomethacrylate, to prepare a dental restorative material, which was then provided for the tests. The results are summarized in Table 5.

COMPARATIVE EXAMPLE 4

2 parts by weight of 3-methacryloxypropyl trimethoxysilane was added to ground products of an alkaline-earth metal aluminoborosilicate glass having a mean particle size of 1 $\mu$m to form a filler. 75 parts by weight of this powder was kneaded under vacuum with 25 parts by weight of a mixed monomer of Bis-MEPP and TEGDMA containing 0.5 part by weight of benzoyl peroxide. After heat polymerization, the resulting powder was subjected to the ball milling to obtain an inorganic-organic composite filler having a mean particle size of 3 $\mu$m. 60 parts by weight of this powder was kneaded under vacuum with 40 parts by weight of a mixed monomer of Bis-MEPP and TEGDMA containing 0.1 part by weight of camphorquinone and 0.5 part by weight of dimethylamino-methacrylate, to prepare a dental restorative material, which was then provided for the tests. The results are summarized in Table 6.

COMPARATIVE EXAMPLE 5

Ground products of an alkaline-earth metal aluminoborosilicate glass having a mean particle size of 1 $\mu$m were capsulated with 10 parts by weight of polymethyl methacrylate by means of a hybridizer manufactured by Nara Machinery Co., Ltd., to form a filler. 60 parts by weight of this powder was kneaded under vacuum with 40 parts by weight of a mixed monomer of Bis-MEPP and TEGDMA containing 0.1 part by weight of camphorquinone and. 0.5 part by weight of dimethylaminomethacrylate, to prepare a dental restorative material, which was then provided for the tests. The results are summarized in Table 6.

COMPARATIVE EXAMPLE 6

As inorganic filler-free organic fillers, a spherical powder of a methyl methacrylate benzyl methacrylate copolymer (mean particle size: 19 μm) was used and provided for fillers. 67 parts by weight of this powder was kneaded under vacuum with 33 parts by weight of a mixed monomer of Bis-MEPP and TEGDMA containing 0.1 part by weight of camphorquinone and 0.5 part by weight of dimethylaminomethacrylate, to prepare a dental restorative material, which was then provided for the tests. The results are summarized in Table 6.

COMPARATIVE EXAMPLE 7

In the preparation of the inorganic-organic composite filler, the same substances as in Example 1 were used, but their compounding ratio was changed to adjust the refractive index. Also, a dental restorative material was prepared by using a mixed monomer of UDMA and TMPTMA in the same manner as in Example 1 and then provided for the tests. The results are summarized in Table 6.

COMPARATIVE EXAMPLE 8

In the preparation of the inorganic-organic composite filler, the same substances as in Example 3 were used, but their compounding ratio was changed to adjust the refractive index. Also, a dental restorative material was prepared by using Bis-MEPP as the monomer in the same manner as in Example 1 and then provided for the tests. The results are summarized in Table 6.

COMPARATIVE EXAMPLE 9

In the preparation of the inorganic-organic composite filler, the same substances as in Example 2 were used, but their compounding ratio was changed. Also, a dental restorative material was prepared in the same manner as in Example 1 and then provided for the tests. The results are summarized in Table 6.

COMPARATIVE EXAMPLES 10 AND 11

In the preparation of the inorganic-organic composite filler, the same substances as in Example 1 were used, but their compounding ratio was changed. Also, dental restorative materials were prepared in the same manner as in Example 1 and then provided for the tests. The results are summarized in Table 7.

COMPARATIVE EXAMPLES 12 AND 13

In the preparation of the inorganic-organic composite filler, the same substances as in Example 1 were used, but their compounding ratio was changed. Dental restorative materials were prepared by using a mixed monomer of Bis-MEPP and TEGDMA in the same manner as in Example 1 and then provided for the tests. The results are summarized in Table 7.

COMPARATIVE EXAMPLES 14 AND 15

In the preparation of the inorganic-organic composite filler, the same substances as in Example 1 were used in the same compounding ratio as in Example 1, but the grinding conditions of the gel were changed. There were thus obtained two kinds of fillers having a different mean particle size. Dental restorative materials were prepared by using a mixed monomer of Bis-MEPP and TEGDMA in the same manner as in Example 1 and then provided for the tests. The results are summarized in Table 7.

Each of the fillers of the foregoing Examples 1 to 25 and Comparative Examples 1 to 15 was subjected to the mean particle size, the refractive index, the inorganic matter content. The dental restorative materials of the foregoing Examples 1 to 25 and Comparative Examples 1 to 15 was subjected to the transparency, the three-point bending strength, the ten-point mean roughness after the polishing, the ten-point surface roughness after the abrasion test, the abrasion depth, and the X-ray contrast properties. The methods are following.

Mean Particle Size

Three spoonfuls of the uniformly mixed filler by a microspatula were charged in a dried 50 ml-beaker, and after adding a dispersion medium (a 0.3 wt % sodium hexametaphosphate aqueous solution), the mixture was stirred. The resulting mixture was irradiated with ultrasonic waves for 3 minutes to prepare a slurry solution. This slurry was measured by means of a laser diffraction type particle size distribution analyzer (SALD-1000, manufactured by Shimadzu Corporation).

Refractive Index (nD)

The filler was charged in a test tube, added with a xylene/heptane/chloronaphthalene mixed liquid having a refractive index lower than the expected refractive index of the filler, and suitably added and mixed with a mixed liquid having a refractive index higher than the expected refractive index, and the slurry was observed under the D-line of sodium. When the refractive index of the liquid came to close to the index of the filler, the powder disapeared apparently. The liquid with this index was prepared again, and several kinds of mixed liquids each having a different refractive index by about 0.002 from other were prepared. These liquids individually added in the test tubes charged with the filler, followed by comparison. Among them, the liquid giving the highest transparency was measured with respect to the refractive index by means of an Abbe refractometer, and the value was determined as the refractive index of the sample powder. The measurement was carried out at a temperature of 23° C. and at a relative humidity of 50%.

Inorganic Matter Content

The filler was precisely weighed in a ceramic crucible having constant weight by firing at 700° C. The temperature was elevated from room temperature to 700° C. over 3 hours, keeping the temperture for 2 hours to burn out the organic matters. The operation for making the constant weight was repeated and accomplished with a precision of 0.2 mg. After the burning out, the percentage of the value of the weight which had been made constant to the sample weight was determined as the inorganic matter content.

Transparency

The dental restorative material was filled in a mold having an inner diameter of 20 mm and a thickness of 1 mm, brought into press contact with a glass plate via a cellophane foil, and irradiated with a light by means of a visible light irradiator (Labolight LV-II, manufactured by GC CORPORATION) for 5 minutes. After polishing with an emery paper #600, the resulting sample surface was polished successively with a slurry of water and a polishing sand (fine) for the prosthodontics and a slurry of water and alumina (0.3 μm) for the finish polishing, whereby the surface was finished in a thickness of (1.00±0.01)mm. Sunream (manufactured by Daiwa Lighting Co., Ltd.) was used as the light source. The distance between the light source and the surface of sample was 1 m. A photodiode array type spectrophotometer (Spectra Scan PR650, manufactured by Photo Research Co., Ltd.) was used as the colorimeter, and the center Φ3 mm of the sample surface on the light trap or standard white board (magnesium oxide) was measured at an angle of 45° against the direction of the sample surface. L*(black) and L*(white) in the CIE-L*a*b* color specification system were calculated and substituted for (L*(white)-L*(black))/L*(white), whereby an index for the transparency was obtained.

Bending Strength

The dental restorative material was filled in a mold having a size of 2×2×25 mm, brought into press contact with a glass plate via a cellophane foil, and irradiated with a light by means of a visible light irradiator (New Light VL-II, manufactured by GC CORPORATION) from the upper direction in one side for 60 seconds such that the whole was exposed. The obtained specimens were soaked in distilled water at 37° C. for 24 hours and then subjected to the three-point bending test by means of an Autograph (manufactured by Shimadzu Corporation) at a span of 20 mm and a crosshead speed of 1 mm/min.

Ten-Point Mean Roughness

The dental restorative material was filled in a mold having an inner diameter of 20 mm and a thickness of 2 mm, brought into press contact with a glass plate via a cellophane foil, and irradiated with a light by means of a visible light irradiator (New Light VL-II, manufactured by GC CORPORATION) from the upper direction in one side for 60 seconds such that the whole was exposed. After polishing the irradiated surface with an emery paper #600, the resulting surface was polished successively with a slurry of water and a polishing sand (fine) for the prosthodontics and a slurry of water and alumina (0.3 μm) for the finish polishing. The finish polished surface was measured with respect to the ten-point mean roughness by means of a surface roughness tester (manufactured by Kosaka Laboratory Ltd.).

Toothbrush Abrasion

The dental restorative material was filled in a mold having an inner diameter of 10 mm and a thickness of 2 mm, brought into press contact with a glass plate via a cellophane foil, and irradiated with a light by means of a visible light irradiator (New Light VL-II, manufactured by GC CORPORATION) from the upper direction on one side for 60 seconds such that the whole was exposed. After polishing the irradiated surface with an emery paper #600, the resulting surface was polished successively with a slurry of water and a polishing sand (fine) for the prosthodontics and a slurry of water and alumina (0.3 μm) for the finish polishing. The specimen was fixed to the tester, a half part of the finish polished surface was masked by a plate of stainless steel having a thickness of 0.1 mm, and a toothbrush was reciprocally moved 10,000 times at a sliding distance of 50 mm and with a load of 500 gf in an aqueous slurry of a toothpaste (trade name: White & White, manufactured by Lion Corporation). After the testing, the abraded surface of the specimen was measured with respect to the abrasion depth by the profile measurement as well as the ten-point mean roughness by means of a surface roughness tester (manufactured by Kosaka Laboratory Ltd.).

Compressive Attrition

A stainless steel frame in which the inner part thereof was comprised of a cone having a basal part of Φ6 mm×H2 mm, a testing surface of Φ2.1 mm×H1 mm, and an intermediate part of H2 mm (total height: 5 mm) was placed on a glass plate such that the testing surface facing downward, and about a half of the dental restorative material was filled therein and irradiated with a light by means of a visible light irradiator (New Light VL-II, manufactured by GC CORPORATION) for 60 seconds. Subsequently, the dental restorative material was filled up to the basal part, brought into, press contact with a glass plate via a cellophane foil, and irradiated with a light for 60 seconds. Further, after the irradiation with a light from the testing surface for 30 seconds, the specimen released from the mold was soaked in distilled water at 37° C. for 24 hours. The specimens were installed in an abrasion tester and reciprocally moved right and left on an emery paper (#600→#1000) to obtain a parallel plane between the basal surface and the testing surface. The specimens were once detached, the basal part of which were then covered by a silicone impressive material, and dipped in a 0.1N-NaOH aqueous solution at 37° C. for 6 days. The specimens washed with distilled water were measured with respect to the height by means of a micrometer and then installed in the abrasion tester. A polisher comprising a spherical powder of polymethyl methacrylate (under 250 μm) and glycerin (1/1 (w/v)) was poured onto a scratched cloth laminated on a parallel glass plate. The specimens were applied with a load of 8.84 kgf/cm$^2$ and subjected to the compressive sliding movement for 100,000 cycles at a rate of 130 cycles per minute, in which the right and left reciprocal movement (sliding distance: 25 mm) following one up and down movement was determined as one cycle. After the testing, the height of the specimens were measured, and the differences before and after the testing were determined as the abrasion amounts. The ten-point mean roughness on the specimens after the testing were also measured.

X-ray Contrast Properties

The testing was carried out in accordance with ISO4049-1988. That is, the specimen having the same thickness as an aluminum disc was exposed on the same X-ray film, and the comparison was made with respect to the contrast properties.

TABLE 1

| | Inorganic-Organic Composite Fillers | | | | | | | | | | | | | | Dental Restorative Materials | | | | | | | |
|---|---|---|---|---|---|---|---|---|---|---|---|---|---|---|---|---|---|---|---|---|---|---|
| | TEOS (g) | M¹ (g) | M² (g) | HCl (g) | NH₃ (g) | H₂O (g) | $\frac{a}{(a+b)}$ | $\frac{c}{(a+b)}$ | i | j | Organic Compounds | Mean Particle Size (μm) | Refractive Index (nD) | Inorganic Matter Content (wt %) | Transparency | Bending Strength (MPa) | Ten-Point Mean Roughness (μm) | Toothbrush Abrasion Depth (μm) | Toothbrush Abrasion Roughness (μm) | Compressive Attrition Depth (μm) | Compressive Attrition Roughness (μm) | X-Ray Contrast Properties | Characteristics |
| Example 1 | 208.3 | — | 3MtP TMeS 62.09 | 0.410 | 0.383 | 103.6 | 0.0 | 0.25 | 0 | 1 | BisMEPP/TEGDMA = 9/1 43.32 | 5.3 | 1.496 | 49.7 | 0.77 | 137 (13) | 0.17 (0.02) | 2.6 (0.5) | 0.30 (0.07) | 3.1 (0.4) | 0.23 (0.09) | Less than aluminum having the same thickness | Superior in mechanical properties and transparency as well as in surface smoothness |
| Example 2 | 197.9 | Ti OiPr 14.21 | 3MtP TMeS 62.09 | 0.392 | 0.366 | 85.57 | 0.05 | 0.25 | 0 | 1 | BisMEPP/TEGDMA = 9/1 44.30 | 5.2 | 1.505 | 50.7 | 0.73 | 141 (11) | 0.20 (0.03) | 2.1 (0.3) | 0.27 (0.06) | 2.6 (0.2) | 0.25 (0.11) | Less than aluminum having the same thickness | Superior in mechanical properties and transparency as well as in surface smoothness |
| Example 3 | 197.9 | Zr OnBu 19.18 | 3MtP TMeS 62.09 | 0.392 | 0.366 | 85.57 | 0.05 | 0.25 | 0 | 1 | BisMEPP/TEGDMA = 9/1 46.47 | 5.9 | 1.512 | 48.9 | 0.67 | 143 (13) | 0.18 (0.03) | 2.2 (0.2) | 0.24 (0.07) | 2.5 (0.5) | 0.26 (0.07) | More than aluminum having the same thickness | Superior in mechanical properties and transparency as well as in surface smoothness |
| Example 4 | 197.9 | Y OiPr 13.31 | 3MtP TMeS 62.09 | 0.392 | 0.366 | 84.67 | 0.05 | 0.25 | 0 | 1 | BisMEPP/TEGDMA = 9/1 45.96 | 5.3 | 1.505 | 49.3 | 0.74 | 140 (11) | 0.22 (0.04) | 2.4 (0.3) | 0.27 (0.08) | 2.1 (0.3) | 0.29 (0.09) | More than aluminum having the same thickness | Superior in mechanical properties and transparency as well as in surface smoothness |
| Example 5 | 197.9 | La OiPr 15.81 | 3MtP TMeS 62.09 | 0.392 | 0.366 | 84.67 | 0.05 | 0.25 | 0 | 1 | BisMEPP/TEGDMA = 9/1 48.46 | 5.2 | 1.509 | 51.2 | 0.76 | 143 (16) | 0.18 (0.02) | 2.8 (0.4) | 0.24 (0.11) | 2.0 (0.3) | 0.29 (0.08) | More than aluminum having the same thickness | Superior in mechanical properties and transparency as well as in surface smoothness |
| Example 6 | 197.9 | Ta OEt 20.31 | 3MtP TMeS 62.09 | 0.392 | 0.366 | 86.47 | 0.05 | 0.25 | 0 | 1 | BisMEPP/TEGDMA = 9/1 51.36 | 6.4 | 1.511 | 49.4 | 0.72 | 131 (19) | 0.20 (0.03) | 2.5 (0.4) | 0.28 (0.09) | 2.4 (0.6) | 0.31 (0.08) | More than aluminum having the same thickness | Superior in mechanical properties and transparency as well as in surface smoothness |

(Note) The numerals in the parentheses show a standard deviation.

TABLE 2

| | Inorganic-Organic Composite Fillers | | | | | | | | | | | | | Dental Restorative Materials | | | | | | | |
|---|---|---|---|---|---|---|---|---|---|---|---|---|---|---|---|---|---|---|---|---|---|
| | TEOS (g) | M¹ (g) | M² (g) | HCl (g) | NH₃ (g) | H₂O (g) | $\frac{a}{(a+b)}$ | $\frac{c}{(a+b)}$ | i | j | Organic Compounds | Mean Particle Size (μm) | Refractive Index (nD) | Inorganic Matter Content (wt %) | Transparency | Bending Strength (MPa) | Ten-Point Mean Roughness (μm) | Toothbrush Abrasion Depth (μm) / Roughness (μm) | | Compressive Attrition Depth (μm) / Roughness (μm) | | X-Ray Contrast Properties | Characteristics |
| Example 7 | 197.9 | Al OiPr 10.21 | 3MtP TMeS 62.09 | 0.392 | 0.366 | 84.67 | 0.05 | 0.25 | 0 | 1 | BisMEPP/ TEGDMA = 9/1 42.86 | 5.2 | 1.497 | 49.5 | 0.72 | 126 (13) | 0.19 (0.02) | 2.9 (0.5) | 0.25 (0.06) | 2.8 (0.3) | 0.22 (0.06) | More than aluminum having the same thickness | Superior in mechanical properties and transparency as well as in surface smoothness |
| Example 8 | 177.1 | Ti OiPr 14.21 Zr OnBu 38.37 | 3MtP TMeS 62.09 | 0.355 | 0.332 | 85.6 | 0.15 | 0.25 | 0 | 1 | BisMEPP/ TEGDMA = 9/1 50.62 | 5.3 | 1.539 | 50.3 | 0.64 | 141 (11) | 0.17 (0.02) | 1.9 (0.3) | 0.24 (0.06) | 2.1 (0.3) | 0.21 (0.09) | More than aluminum having the same thickness | Superior in mechanical properties and transparency as well as in surface smoothness |
| Example 9 | 31.25 | Y OiPr 13.31 La OiPr 15.81 | 3MtP TMeS 15.52 | 0.066 | 0.092 | 19.6 | 0.40 | 0.25 | 0 | 1 | MMA 197.3 | 26 | 1.517 | 10.2 | 0.73 | 121 (10) | 0.12 (0.02) | 3.2 (0.4) | 0.20 (0.04) | 1.7 (0.2) | 0.20 (0.03) | Equal to aluminum having the same thickness | Superior in mechanical properties and transparency as well as in surface smoothness |
| Example 10 | 21.88 | Al OiPr 18.38 Ti OiPr 17.06 Zr OnBu 17.26 | 3MtP TMeS 18.63 | 0.052 | 0.110 | 24.1 | 0.65 | 0.25 | 0 | 1 | MMA 93.42 | 30 | 1.544 | 19.3 | 0.66 | 119 (12) | 0.11 (0.03) | 3.6 (0.4) | 0.19 (0.05) | 1.4 (0.2) | 0.22 (0.03) | More than aluminum having the same thickness | Superior in mechanical properties and transparency as well as in surface smoothness |

(Note) The numerals in the parentheses show a standard deviation.

TABLE 3

Inorganic-Organic Composite Fillers

| | TEOS (g) | M¹ (g) | M² (g) | HCl (g) | NH₃ (g) | H₂O (g) | $\frac{a}{(a+b)}$ | $\frac{c}{(a+b)}$ | i | j | Organic Compounds | Mean Particle Size (μm) | Refractive Index (nD) | Inorganic Matter Content (wt %) | Transparency |
|---|---|---|---|---|---|---|---|---|---|---|---|---|---|---|---|
| Example 11 | 197.9 | Zr OnBu 19.18 | 3MtP TMeS 4.97 | 0.355 | 0.332 | 73.14 | 0.05 | 0.02 | 0 | 1 | BisMEPP/ TEGDMA = 9/1 13.56 | 0.77 | 1.507 | 79.4 | 0.73 |
| Example 12 | 19.79 | Zr OnBu 1.918 | 3MtP TMeS 74.5 | 0.089 | 0.083 | 23.41 | 0.05 | 3.0 | 0 | 1 | MMA/ BZMA = 9/1 59.25 | 17 | 1.521 | 21.1 | 0.64 |
| Example 13 | 187.5 | Zr OnBu 38.37 | 3MtP TMeS 24.84 | 0.346 | 0.324 | 77.46 | 0.10 | 0.10 | 0 | 1 | BisMEPP/ TEGDMA = 9/1 18.31 | 0.9 | 1.531 | 70.3 | 0.61 |
| Example 14 | 166.7 | Ta OEt 81.25 | 3MtP TMeS 24.84 | 0.310 | 0.290 | 81.07 | 0.20 | 0.10 | 0 | 1 | BisMEPP/ TEGDMA = 9/1 29.40 | 1.1 | 1.580 | 68.9 | 0.51 |
| Example 15 | 72.92 | Al OiPr 71.49 Y OiPr 26.62 La OiPr 63.23 | 3MtP TMeS 24.84 | 0.146 | 0.366 | 42.3 | 0.65 | 0.10 | 0 | 1 | UDMA/ TEGDMA = 1/1 76.03 | 5.3 | 1.598 | 50.6 | 0.49 |

Dental Restorative Materials

| | Bending Strength (MPa) | Ten-Point Mean Roughness (μm) | Toothbrush Abrasion Depth (μm) | Toothbrush Abrasion Roughness (μm) | Compressive Attrition Depth (μm) | Compressive Attrition Roughness (μm) | X-Ray Contrast Properties | Characteristics |
|---|---|---|---|---|---|---|---|---|
| Example 11 | 149 (23) | 0.26 (0.03) | 2.5 (0.4) | 0.28 (0.09) | 3.3 (0.6) | 0.32 (0.04) | More than aluminum having the same thickness | Superior in mechanical properties and transparency as well as in surface smoothness |
| Example 12 | 123 (9) | 0.13 (0.02) | 3.9 (0.7) | 0.27 (0.07) | 1.9 (0.2) | 0.22 (0.03) | Equal to aluminum having the same thickness | Superior in mechanical properties and transparency as well as in surface smoothness |
| Example 13 | 140 (16) | 0.22 (0.03) | 2.7 (0.4) | 0.33 (0.10) | 2.3 (0.4) | 0.26 (0.07) | More than aluminum having the same thickness | Superior in mechanical properties and transparency as well as in surface smoothness |
| Example 14 | 137 (14) | 0.25 (0.04) | 2.9 (0.3) | 0.29 (0.08) | 3.1 (0.6) | 0.33 (0.09) | More than aluminum having the same thickness | Superior in mechanical properties and transparency as well as in surface smoothness |
| Example 15 | 127 (11) | 0.16 (0.03) | 3.2 (0.4) | 0.19 (0.02) | 1.2 (0.2) | 0.23 (0.05) | More than aluminum having the same thickness | Superior in mechanical properties and transparency as well as in surface smoothness |

TABLE 4

| | Inorganic-Organic Composite Fillers | | | | | | | | | | | | Dental Restorative Materials | | | | | | | |
|---|---|---|---|---|---|---|---|---|---|---|---|---|---|---|---|---|---|---|---|---|
| | TEOS (g) | $M^1$ (g) | $M^2$ (g) | HCl (g) | $NH_3$ (g) | $H_2O$ (g) | $\frac{a}{(a+b)}$ | $\frac{c}{(a+b)}$ | i | j | Organic Compounds | Mean Particle Size (μm) | Refractive Index (nD) | Inorganic Matter Content (wt %) | Transparency | Bending Strength (MPa) | Ten-Point Mean Roughness (μm) | Toothbrush Abrasion Depth (μm) / Roughness (μm) | Compressive Attrition Depth (μm) / Roughness (μm) | X-Ray Contrast Properties | Characteristics |
| Example 16 | 208.3 | — | 3MtP TMeS 62.09 | 0.410 | 0.383 | 103.6 | 0.0 | 0.25 | 0 | 1 | BisMEPP/ TEGDMA = 9/1 43.32 | 0.1 | 1.496 | 49.7 | 0.72 | 130 (9) | 0.12 (0.02) | 2.9 (0.4) / 0.26 (0.07) | 1.9 (0.2) / 0.19 (0.06) | Less than aluminum having the same thickness | Superior in mechanical properties and transparency as well as in surface smoothness |
| Example 17 | 208.3 | — | 3MtP TMeS 62.09 | 0.410 | 0.383 | 103.6 | 0.0 | 0.25 | 0 | 1 | BisMEPP/ TEGDMA = 9/1 43.32 | 48 | 1.496 | 49.7 | 0.78 | 124 (12) | 0.14 (0.04) | 3.2 (0.5) / 0.29 (0.06) | 1.5 (0.4) / 0.22 (0.03) | Less than aluminum having the same thickness | Superior in mechanical properties and transparency as well as in surface smoothness |
| Example 18 | 208.3 | — | 3MtP MD-MeS 58.09 | 0.410 | 0.383 | 81.1 | 0.0 | 0.25 | 1 | 1 | BisMEPP/ TEGDMA = 9/1 39.56 | 7.7 | 1.494 | 50.9 | 0.74 | 131 (12) | 0.09 (0.02) | 4.3 (0.5) / 0.19 (0.06) | 1.1 (0.3) / 0.21 (0.01) | Less than aluminum having the same thickness | Superior in mechanical properties and transparency as well as in surface smoothness |
| Example 19 | 208.3 | — | 3GP TMeS 59.08 | 0.365 | 0.341 | 85.3 | 0.0 | 0.25 | 0 | 1 | BisGPhP 16.28 P-Amide 30.04 | 9.2 | 1.462 | 49.6 | 0.61 | 121 (10) | 0.15 (0.02) | 3.3 (0.5) / 0.25 (0.10) | 0.9 (0.3) / 0.22 (0.04) | Less than aluminum having the same thickness | Superior in mechanical properties and transparency as well as in surface smoothness |
| Example 20 | 187.5 | Zr OnBu 38.37 | 3AP TMeS 17.93 | 0.328 | 0.307 | 77.46 | 0.10 | 0.10 | 0 | 1 | GMA 14.22 BisMEPP/ TEGDMA = 9/1 52.38 | 7.8 | 1.533 | 48.9 | 0.59 | 131 (9) | 0.19 (0.04) | 3.3 (0.7) / 0.36 (0.08) | 1.9 (0.3) / 0.28 (0.05) | More than aluminum having the same thickness | Superior in mechanical properties and transparency as well as in surface smoothness |

(Note) The numerals in the parentheses show a standard deviation.

TABLE 5

| | Inorganic-Organic Composite Fillers | | | | | | | | | | | Dental Restorative Materials | | | | | | | | | |
|---|---|---|---|---|---|---|---|---|---|---|---|---|---|---|---|---|---|---|---|---|---|
| | TEOS (g) | M¹ (g) | M² (g) | HCl (g) | NH₃ (g) | H₂O (g) | $\frac{a}{(a+b)}$ | $\frac{c}{(a+b)}$ | i | j | Organic Compounds | Mean Particle Size (μm) | Refractive Index (nD) | Inorganic Matter Content (wt %) | Transparency | Bending Strength (MPa) | Ten-Point Mean Roughness (μm) | Toothbrush Abrasion Depth (μm) / Roughness (μm) | Compressive Attrition Depth (μm) / Roughness (μm) | X-Ray Contrast Properties | Characteristics |
| Example 21 | 187.5 | Zr OnBu 38.37 | 3McP TMeS 49.08 | 0.374 | 0.349 | 85.6 | 0.10 | 0.25 | 0 | 1 | BisMEPP/ TEGDMA = 9/1 62.63 | 8.5 | 1.530 | 51.1 | 0.59 | 119 (16) | 0.11 (0.04) | 4.8 (1.3) / 0.32 (0.07) | 1.1 (0.3) / 0.19 (0.04) | More than aluminum having the same thickness | Superior in mechanical properties and transparency as well as in surface smoothness |
| Example 22 | 208.3 | — | Ph-TMeS 99.15 | 0.365 | 0.341 | 99.1 | 0.0 | 0.50 | 1 | 2 | 1,3BG 45.06 | 6.8 | 1.460 | 52.0 | 0.53 | 131 (12) | 0.22 (0.04) | 3.3 (0.4) / 0.31 (0.04) | 2.3 (0.4) / 0.29 (0.08) | Less than aluminum having the same thickness | Superior in mechanical properties and transparency as well as in surface smoothness |
| Example 23 | 104.2 | — | DPh DMeS 244.3 | 0.182 | 0.255 | 72.1 | 0.0 | 2.0 | 2 | 1 | 1,3BG 45.06 | 7.1 | 1.502 | 31.1 | 0.71 | 121 (10) | 0.11 (0.02) | 4.1 (0.3) / 0.22 (0.02) | 1.5 (0.2) / 0.19 (0.04) | Less than aluminum having the same thickness | Superior in mechanical properties and transparency as well as in surface smoothness |
| Example 24 | 187.5 | Zr OnBu 38.37 | IPT-MtT 36.22 | 0.334 | 0.312 | 73.8 | 0.10 | 0.10 | 0 | 3 | UDMA/ TEGDMA = 1/1 86.05 | 14 | 1.536 | 40.1 | 0.63 | 122 (11) | 0.11 (0.04) | 4.1 (0.8) / 0.33 (0.05) | 1.5 (0.6) / 0.22 (0.05) | More than aluminum having the same thickness | Superior in mechanical properties and transparency as well as in surface smoothness |
| Example 25 | 187.5 | Zr OnBu 38.37 | IPTAT TMeS 41.64 | 0.334 | 0.312 | 73.8 | 0.10 | 0.10 | 0 | 3 | GMA 42.65 | 23 | 1.505 | 37.5 | 0.74 | 111 (8) | 0.08 (0.03) | 5.5 (1.2) / 0.38 (0.10) | 2.2 (0.4) / 0.18 (0.05) | More than aluminum having the same thickness | Superior in mechanical properties and transparency as well as in surface smoothness |
| Comparative Example 1 | Commercially available ground products of alkaline earth metal aluminoborosilicate glass | | | | | | | | — | — | — | 0.9 | 1.530 | 100 | 0.69 | 138 (18) | 0.18 (0.06) | 1.1 (0.8) / 0.78 (0.12) | 21 (3.1) / 1.2 (0.4) | More than aluminum having the same thickness | Inferior in surface smoothness |
| Comparative Example 2 | 208.3 | — | — | — | 34.06 | 180.2 | — | — | — | — | — | 0.6 | 1.452 | 100 | 0.15 | 122 (11) | 0.18 (0.06) | 1.5 (0.8) / 0.45 (0.12) | 28 (3.1) / 0.78 (0.08) | Less than aluminum having the same thickness | Inferior in transparency |

TABLE 5-continued

| | Inorganic-Organic Composite Fillers | | | | | | | | | | | Dental Restorative Materials | | | | | | | | |
|---|---|---|---|---|---|---|---|---|---|---|---|---|---|---|---|---|---|---|---|---|
| | TEOS (g) | M¹ (g) | M² (g) | HCl (g) | NH₃ (g) | H₂O (g) | $\frac{a}{a+b}$ | $\frac{c}{a+b}$ | i | j | Organic Compounds | Mean Particle Size (μm) | Refractive Index (nD) | Inorganic Matter Content (wt %) | Transparency | Bending Strength (MPa) | Ten-Point Mean Roughness (μm) | Toothbrush Abrasion Depth (μm) / Roughness (μm) | Compressive Attrition Depth (μm) / Roughness (μm) | X-Ray Contrast Properties | Characteristics |
| Comparative Example 3 | Commercially available colloidal silica (Aerosil R972) | | | | | | | | — | — | — | 0.016 | 1.450 | 98.3 | 0.68 | 102 (4) | 0.11 (0.03) | 26 (5.1) / 0.85 (0.11) | 10 (3) / 0.25 (0.06) | Less than aluminum having the same thickness | Inferior in mechanical properties |

(Note) The numerals in the parentheses show a standard deviation.

TABLE 6

| | Inorganic-Organic Composite Fillers | | | | | | | | | | Dental Restorative Materials | | | | | | | | | |
|---|---|---|---|---|---|---|---|---|---|---|---|---|---|---|---|---|---|---|---|---|
| | TEOS (g) | M¹ (g) | M² (g) | HCl (g) | NH₃ (g) | H₂O (g) | $\frac{a}{(a+b)}$ | $\frac{c}{(a+b)}$ | i | j | Organic Compounds | Mean Particle Size (μm) | Refractive Index (nD) | Inorganic Matter Content (wt %) | Transparency | Bending Strength (MPa) | Ten-Point Mean Roughness (μm) | Toothbrush Abrasion Depth (μm) / Roughness (μm) | Compressive Attrition Depth (μm) / Roughness (μm) | X-Ray Contrast Properties | Characteristics |
| Comparative Example 4 | Kneading of commercially available ground products of alkaline earth metal aluminoborosilicate glass/monomers → Heat Polymerization → Grinding | | | | | | | | | | BisMEPP/TEGDMA = 1/1 | 7.1 | 1.530 | 75 | 0.56 | 108 (5) | 0.12 (0.05) | 1.1 (0.8) / 0.83 (0.08) | 18 (1.9) / 0.81 (0.09) | More than aluminum having the same thickness | Inferior in surface smoothness |
| Comparative Example 5 | Commercially available ground products of alkaline earth metal aluminoborosilicate glass/capsulated power of PMMA (prepared by the mechanofusion) | | | | | | | | | | PMMA | 1.2 | Opaque | 91 | 0.21 | 105 (18) | 0.23 (0.04) | 2.2 (0.6) / 0.74 (0.11) | 26 (2.2) / 1.0 (0.3) | More than aluminum having the same thickness | Inferior in transparency and surface smoothness |
| Comparative Example 6 | PMMA/PBZ (pearl powder) | | | | | | | | — | — | — | 19 | 1.522 | 0.0 | 0.58 | 92 (5) | 0.08 (0.02) | 31 (4.4) / 0.46 (0.15) | 8.1 (1.1) / 0.33 (0.04) | Less than aluminum having the same thickness | Inferior in mechanical properties |
| Comparative Example 7 | 208.3 | — | 3MtP TMeS 4.97 | 0.368 | 0.344 | 73.1 | 0.0 | 0.02 | 0 | 1 | UDMA 12.78 | 7.1 | 1.458 | 78.9 | 0.21 | 108 (6) | 0.08 (0.02) | 3.8 (0.8) / 0.34 (0.12) | 1.3 (0.4) / 0.22 (0.03) | Less than aluminum having the same thickness | Inferior in transparency |
| Comparative Example 8 | 72.92 | AL OiPr 71.49 Y OiPr 26.62 La OiPr 63.23 | 3MtP TMeS 24.84 | 0.146 | 0.366 | 42.3 | 0.65 | 0.10 | 0 | 1 | BisMEPP/TEGDMA = 4/6 76.03 | 7.8 | 1.611 | 50.2 | 0.19 | 131 (13) | 0.22 (0.05) | 4.2 (0.2) / 0.22 (0.03) | 1.4 (0.3) / 0.33 (0.06) | More than aluminum having the same thickness | Inferior in transparency |
| Comparative Example 9 | 65.5 | Ti OiPr 199.0 | 3MtP TMeS 62.09 | 0.155 | 0.290 | 85.57 | 0.70 | 0.25 | 0 | 1 | BisMEPP/TEGDMA = 9/1 57.17 | 6.7 | Opaque | 49.6 | 0.13 | 131 (13) | 0.18 (0.04) | 2.5 (0.4) / 0.33 (0.05) | 4.9 (0.3) / 0.66 (0.14) | Less than aluminum having the same thickness | Inferior in transparency |

(Note) The numerals in the parentheses show a standard deviation.

TABLE 7

| | Inorganic-Organic Composite Fillers | | | | | | | | | | | | | Dental Restorative Materials | | | | | | | |
|---|---|---|---|---|---|---|---|---|---|---|---|---|---|---|---|---|---|---|---|---|---|
| | TEOS (g) | M¹ (g) | M² (g) | HCl (g) | NH₃ (g) | H₂O (g) | $\frac{a}{a+b}$ | $\frac{c}{(a+b)}$ | i | j | Organic Compounds | Mean Particle Size (μm) | Refractive Index (nD) | Inorganic Matter Content (wt %) | Transparency | Bending Strength (MPa) | Ten-Point Mean Roughness (μm) | Toothbrush Abrasion Depth (μm) | Toothbrush Abrasion Roughness (μm) | Compressive Attrition Depth (μm) | Compressive Attrition Roughness (μm) | X-Ray Contrast Properties | Characteristics |
| Comparative Example 10 | 208.3 | — | 3MtP TMeS 2.48 | 0.366 | 0.342 | 72.60 | 0.0 | 0.01 | 0 | 1 | BisMEPP/ TEGDMA = 9/1 13.90 | 2.8 | Opaque | 78.9 | 0.11 | 134 (13) | 0.26 (0.06) | 2.2 (0.6) | 0.29 (0.06) | 7.9 (0.8) | 0.77 (0.11) | Less than aluminum having the same thickness | Inferior in transparency |
| Comparative Example 11 | 20.83 | — | 3MtP TMeS 99.34 | 0.109 | 0.102 | 28.82 | 0.0 | 4.0 | 0 | 1 | BisMEPP/ TEGDMA = 9/1 69.27 | 15 | 1.488 | 21.0 | 0.65 | 110 (8) | 0.09 (0.02) | 35 (2.5) | 4.5 (0.89) | 4.5 (0.4) | 0.44 (0.07) | Less than aluminum having the same thickness | Inferior in mechanical properties, particularly toothbrush abrasion |
| Comparative Example 12 | 20.83 | — | 3MtP TMeS 24.84 | 0.055 | 0.051 | 12.61 | 0.0 | 1.0 | 0 | 1 | BisMEPP/ TEGDMA = 1/1 146.9 | 11 | 1.528 | 6.8 | 0.63 | 112 (8) | 0.08 (0.02) | 23 (0.9) | 2.2 (0.23) | 1.8 (0.2) | 0.23 (0.04) | Less than aluminum having the same thickness | Inferior in mechanical properties, particularly toothbrush abrasion |
| Comparative Example 13 | 208.3 | — | 3MtP TMeS 4.97 | 0.368 | 0.344 | 73.14 | 0.0 | 0.02 | 0 | 1 | BisMEPP/ TEGDMA = 9/1 8.27 | 0.7 | 1.517 | 85.2 | 0.57 | 122 (13) | 0.22 (0.03) | 2.3 (0.3) | 0.82 (0.23) | 22 (1.5) | 0.56 (0.10) | Less than aluminum having the same thickness | Inferior in surface smoothness and compressive attrition |
| Comparative Example 14 | 208.3 | — | 3MtP TMeS 62.09 | 0.410 | 0.383 | 103.6 | 0.0 | 0.25 | 0 | 1 | BisMEPP/ TEGDMA = 9/1 43.32 | 0.05 | 1.492 | 49.7 | 0.53 | 105 (11) | 0.15 (0.02) | 35 (2.5) | 4.5 (0.89) | 4.5 (0.4) | 0.44 (0.07) | Less than aluminum having the same thickness | Inferior in mechanical properties, particularly toothbrush abrasion |
| Comparative Example 15 | 208.3 | — | 3MtP TMeS 62.09 | 0.410 | 0.383 | 103.6 | 0.0 | 0.25 | 0 | 1 | BisMEPP/ TEGDMA = 9/1 43.32 | 109 | 1.496 | 49.7 | 0.68 | 141 (14) | 0.22 (0.02) | 2.6 (0.5) | 0.30 (0.07) | 56 (4.1) | 3.8 (0.42) | Less than aluminum having the same thickness | Inferior in mechanical properties, particularly compressive attrition |

(Note) The numerals in the parentheses show a standard deviation.

As is clear from the results shown in the Tables, the dental inorganic-organic composite filler according to the present invention is provided with superior effects, particularly when it is used for dental restorative materials, such that it has a superior mechanical strength and abrasion resistance and a suitable consistency and handling, shows a coefficient of thermal expansion close to the teeth and a low polymerization shrinkage value, and exhibits a suitable transparency and surface smoothness in the oral cavity. Therefore, the present invention will greatly contribute to the dental treatment.

While the invention has been described in detail and with reference to specific embodiments thereof, it will be apparent to one skilled in the art that various changes and modifications can be made therein without departing from the spirit and scope thereof.

What is claimed is:

1. Dental inorganic-organic composite fillers having a mean particle size of from 0.1 to 50 μm which do not scatter a visible light of from 360 to 830 nm in the particles thereof, have a refractive index nD by the D-line of sodium in the range of 1.460≦nD≦1.600, and which are obtained by grinding a material represented by the following mean empirical formula:

$$aM^1O_{x/2} \cdot bSiO_2 \cdot cM^2O_{(4-i-j)/2}R^1_i R^2_j$$

wherein

M$^1$ is one or more members selected from the group consisting of Ti, Zr, Y, La, Ta and Al, which is bonded to Si or M$^2$ via the crosslinked oxygen; and x is a valence of M$^1$;

M$^2$ is Si and/or Ti;

R$^1$ is a non-reactive group; and

R$^2$ is an organic reactive group having been reacted with an organic compound;

i is 0, 1, or 2; and j is 1, 2, or 3, provided that i and j are satisfied with 1≦(i+j)≦3; and a, b, and c are each a molar ratio, provided that a, b, and c are satisfied by 0≦a/(a+b)≦0.65 and 0.02≦c/(a+b)≦3.0.

2. Dental inorganic-organic composite fillers as claimed in claim 1, having an inorganic matter content in the range of from 10 to 80% by weight.

3. Dental inorganic-organic composite fillers as claimed in claim 1, wherein when M$^2$ is Si, then R$^2$ is an organic compound reacted with a reactive group selected from the group consisting of an unsaturated double bond, a glycidoxyl group, an amino group, a mercapto group, and an alkoxyl group; when M$^2$ is Ti, then R$^2$ is an organic compound reacted with a reactive group selected from the group consisting of an unsaturated double bond and an amino group; and R$^1$ is a phenyl group and/or a non-reactive group represented by $C_nH_{2n+1}$, wherein n is from 1 to 10.

4. Dental inorganic-organic composite fillers as claimed in claim 1, wherein M$^1$ is one or more members selected from the group consisting of Zr, Y, La, and Ta; and a and b are satisfied with 0.10≦a/(a+b)≦0.65.

5. Dental inorganic-organic composite fillers as claimed in claim 1, wherein the surfaces of the particles are modified with a silane coupling agent.

* * * * *